United States Patent [19]

Horwath

[11] Patent Number: 4,473,645
[45] Date of Patent: Sep. 25, 1984

[54] PROCESS FOR PRODUCING THERMALLY STABLE ALPHA-AMYLASE

[75] Inventor: Robert O. Horwath, Westport, Conn.

[73] Assignee: Nabisco Brands, Inc., Parsippany, N.J.

[21] Appl. No.: 480,428

[22] Filed: Mar. 30, 1983

[51] Int. Cl.³ .......................... C12N 9/28; C12R 1/10
[52] U.S. Cl. .................................... 435/202; 435/836
[58] Field of Search ................................ 435/202, 836

[56] References Cited
FOREIGN PATENT DOCUMENTS 1296839 11/1972 United Kingdom ................ 435/202

Primary Examiner—Lionel M. Shapiro
Attorney, Agent, or Firm—Richard Kornutik

[57] ABSTRACT

Improved production of α-amylase is realized by cultivating *B. licheniformis* ATCC No. 39326 in nutrient medium therefor, especially when medium contains lactose.

6 Claims, No Drawings

PROCESS FOR PRODUCING THERMALLY STABLE ALPHA-AMYLASE

This invention relates to an improved process for the production of thermally stable alpha amylase.

Alpha amylases are well known enzymes useful in commercial cleaning products and in the conversion of starch to water-soluble carbohydrates, particularly suited for eventual conversion, either chemical or enzymatic, to glucose, a useful commercial product.

Amylases have been prepared by microbiological processes which involved cultivating species of Bacillus microorganisms. In British patent specification No. 1,296,839 there is described a process for producing thermally stable alpha amylase by cultivating species of *Bacillus licheniformis*. The enzyme so produced is of significantly higher thermal stability than that produced by strains of *Bacillus subtilis* but the yields of enzyme activity reported in the British specification are not high and leave considerable to be desired as far as commercial production of thermally-stable amylase enzyme is concerned.

It has now been discovered that a strain of *B. licheniformis* is particularly adaptable to commercial production of thermally stable alpha amylase in view of the high yields of enzyme activity produced with the said strain. In general, yields of at least about 10 times more than reported in the aforesaid British Specification have been obtained with the present strain of *B. licheniformis*. Viable cultures of this organism have been deposited with the American Type Culture Collection where the organism has been accorded the accession number ATCC 39326.

The alpha amylase produced in accordance with the present invention is of the same order of thermal stability as that produced in accordance with British Specification No. 1,296,839, and is relatively stable in the presence of high concentrations of calcium ion sequestering agents. All functional advantages claimed in the British Specification are present, plus high yields obtained by the present process.

In order to accomplish the desirable results of the present invention, the specified *B. licheniformis* need only be cultivated in a nutrient medium for a period sufficient to result in significant enzyme production. Usually, the fermentation is carried out for from about 2 to 6 days at temperatures ranging from about 25° to 55° C., using the usual sources of assimilable carbon and nitrogen as well as other essential nutrients, all of which are well known to those skilled in the art. Suitable carbon sources include, for example, the carbohydrates, lactose, glucose and starch or carbohydrate-containing materials such as soy, corn meal and the like, and mixtures thereof. The amount of carbohydrate can vary considerable, from about 1% to 25% w/v, preferably from 5% to about 15% w/v.

In the most preferred form of the invention, lactose is employed as the carbon source since best yields of enzyme activity are obtained therewith. Usually, from about 1% to about 20% w/v of lactose is used in the nutrient medium, with from about 5% to about 15% w/v being preferred. Lactose can be used either as the sole carbon source or in conjunction with other sources such as whey and soy flour the latter usually at less than about 5% w/v.

The nitrogen source can be organic or inorganic including, for example, soluble nitrates or ammonium salts. The organic nitrogen sources include yeast extract, cornsteep liquor, peanut meal and the like.

The microorganism is cultivated in the nutrient medium under aerobic conditions which are produced by aerating the fermentation vessels, usually at a rate of about one volume of air per volume of medium.

The enzyme is recovered from the reaction medium after desired levels of enzyme activity are attained. The methods of recovery are well-known to those skilled in the art including for example precipitation of the enzyme using known precipitants such as sodium sulfate or water-miscible organic solvents such as acetone or ethanol. Recovery of the precipitate by centrifuging or filtering followed by drying yields purified solid enzyme.

In addition to the aforementioned microorganism, the present invention contemplates the use of mutants and variants thereof as well as genetically transformed microorganisms derived therefrom by introduction of the enzyme genes into said microorganisms.

The following example further illustrates the invention.

EXAMPLE 1

A. A slant of *B. licheniformis* ATTC 39326 on Difco Starch Agar is streaked onto a Difco Starch Agar plate and grown at 40° C.±1° C. for 18 hrs±1 hour.

B. A loopful of cells is inoculated into the following broth:

| Aqueous Inoculation Broth |
| --- |
| 0.5% Yeast Extract |
| 0.5% Tryptone |
| 0.1% $K_2HPO_4$ |
| 0.1% D-Glucose |
| 350 ml per 1 L flask |

The flask is incubated at 40° C.±1° C. for 1–2 days at 200 rpm on a New Brunswick G-50 shaker (2" orbit).

C. The entire content of the flask is used as inoculum into a final volume of 3150 ml of Fermentor Medium containing the following:

| Aqueous Fermentor Medium |
| --- |
| 10% Lactose* |
| 1.4% $K_2HPO_4$* |
| 0.6% $KH_2PO_4$* |
| 0.6% $(NH_4)_2SO_4$ |
| 0.3% Sodium citrate |
| 3.0% Whole grain soy flour |
| 0.05% $CaCl_2$ $2H_2O$ |
| 1.0 ml Mazu DF 6000 |
| Initial pH = 6.8–7.0 |

*Autoclaved separately from the other ingredients.

The fermentor is autoclaved for 60 min. 121° C., 15 lbs.

To facilitate the optimal production of α-amylase, the pH of the culture medium should be below a pH of 8.0 but not lower than a pH of 5.5.

In order to control possible foaming during propagation, Mazu DF 6000 antifoam is provided through a conventional foam control device.

| Fermentation Conditions |
| --- |
| 600 rpm |
| 40° C. |

| Fermentation Conditions |
|---|
| 1 liter v/v Air |

The pH after 72 hours is usually between 6.5 and 7.0.

Measurement of the alpha amylase enzyme activity is carried out by standard techniques. One such is a modified Wohlegermuth type of method in which the activity is measured in terms of the digestion time to produce a color change denoting a definite stage of dextrinization of starch. The method is calibrated so that the amylase strength can be calculated directly in liquefons per gram as described below.

The liquefon alpha amylase assay procedure used as follows: Prepare sample solution using the 0.025 molar $CaCl_2$ solution as the solvent and diluent, so that 5 ml of the final diluted sample will give a dextrinizing time of about 10 minutes. If the approximate potency of the enzyme preparation is unknown, the proper sample size and/or dilution must be found by trial and error.

Dispense 5.0 ml dilute iodine solution into 13×200 mm test tubes and attemperate in water bath (30° C.). 10 to 12 test tubes.

Transfer 10 ml Lintner starch to a 23×200 mm test tube and attemperate in 30° C. water bath.

Transfer 25–30 ml dilute unknown alpha amylase solution to 23×200 mm test tubes and attemperate in 30° C. water bath.

Transfer 5 ml of the unknown diluted enzyme sample to 10 ml starch solution and start stopwatch when half the unknown alpha amylase solution has been added and then blow the last half of the solution from the pipette.

At appropriate time intervals, add 1 ml (1 ml pipette) of the hydrolyzing mixture (starch, alpha amylase solution) to a test tube containing the attemperated diluted iodine solution. Shake, pour into a 13 mm precision square tube and compare with the standard alpha amylase color disc in the Hellige comparator. The contents of the 1 ml pipette are blown into the iodine solution in order that the end-point time can be more accurately measured. When the time of the end-point is nearly reached, samples should be taken at 0.1 minute intervals (6 to 12 seconds).

Record time and dilution when reaction is complete and calculate activity in liquefons per gram or ml.

The calculation of enzyme activity uses the following formula:

$$\text{Liquefons per gram (or ml.)} = \frac{1140}{\text{Actual weight (or ml.) of sample} \times \text{dextrinizing time in minutes}} \times \text{dilution}$$

The solutions employed in the foregoing assay procedure are prepared as follows:

Starch Solution—Soluble Lintner starch (10 g) is mixed with 35 ml of distilled water in a flask which is then heated to boiling and held for 5 minutes at boiling temperature with constant agitation. Cool to room temperature and add 125 ml of acetate buffer and enough water to bring to 500 ml. Add 1 ml toluene. The stability of this solution is checked with a standard sample of α-amylase of known potency.

Acetate buffer—Weight out 1 mole sodium acetate (82.0 g) and dissolve in 800 ml water. Bring the pH to 6.2,±0.1, with acetic acid and dilute to one liter. Use 20 ml of this in making up one liter of starch substrate.

Calcium Chloride Diluting Solution, 0.025 Molar—Dissolve 11.1 g C.P. anyhydrous calcium chloride in 4 liters of water.

Buffer Solution—Dissolve 25.3 g sodium hydroxide pellets and 340 g potassium dihydrogen phosphate in distilled water and bring to 2 liters in a volumetric flask. When buffer reaches room temperature, make up to volume (pH 6.2,±0.1).

Stock Iodine Solution—Dissolve 5.50 g C.P. iodine crystals and 11.0 g KI in $H_2O$ and dilute to 250 ml. Store in a dark bottle.

Dilute Iodine Solution—Dissolve 20.0 g KI in $H_2O$, add 2.00 ml of stock iodine solution and dilute to 500 ml.

Using the above described liquifon procedure, the enzyme activity in the fermented medium produced in accordance with the example exceeds 1000 liquefons/ml, most often reaching 1500–2000 liquefons/ml. Using this assay method, the *B. licheniformis* cultures described in the British Specification yielded an average of 125 liquefons/ml in the fermentation medium described above, whereas the same cultures yielded even lower activities, i.e., below 50 liquefons/ml, in the medium described in the British Specification.

Another method for measuring alpha amylase activity is a modified SKB procedure described in the British Specification. Under conditions of this test, the cultures of the British Specification produced less than 500 SKB units/ml, whereas by comparison the culture of the present invention produced an activity of about 10,000 SKB units/ml.

What is claimed is:

1. A process for the production of alpha amylase which comprises cultivating *B. licheniformis* ATCC No. 39326 in a nutrient medium therefor to produce the enzyme product.

2. The process according to claim 1 wherein the alpha amylse activity is recovered from the nutrient medium.

3. A process for the production of alpha amylase which comprises cultivating *B. licheniformis* ATCC No. 39326 in a nutrient medium comprising lactose as a carbon source to produce the enzyme product.

4. The process according to claim 3 wherein the level of lactose in the nutrient medium is from about 5% to about 15% w/v.

5. The process according to claim 3 wherein the alpha amylase activity is recovered from the nutrient medium.

6. The process according to claim 3 wherein the pH of said medium is maintained below a pH of 8 but not lower than 5.5.

* * * * *